United States Patent
Chiang

(10) Patent No.: US 6,452,037 B1
(45) Date of Patent: Sep. 17, 2002

(54) MULTIOLIGONANILINATED FULLERENES

(76) Inventor: Long Y. Chiang, 4F, #15, Lane 97, Shin-Sheng S. Road, Sec. 1, Taipei (TW)

( * ) Notice: Subject to any disclaimer, the term of this patent is extended or adjusted under 35 U.S.C. 154(b) by 0 days.

(21) Appl. No.: 09/840,323

(22) Filed: Apr. 23, 2001

(51) Int. Cl.$^7$ .............................................. C07C 69/76
(52) U.S. Cl. ...................................... 560/102; 564/123
(58) Field of Search ........................... 560/102; 564/123

(56) References Cited

PUBLICATIONS

Anantharaj et al, Synthetic Metals, 101, (1997) pp. 791–792.*
Wang et al, Synthetic Metals, 103, (1999) pp. 2350–2353.*
Irie et al, Biosci. Biotec. Biochem., 60 (8), (1996) pp. 1359–1361.*
Anantharaj et al., "Synthesis of Starburst Hexa(oligoanilinated) $C_{60}$ Using Hexanitrol[60]fullerene as a Precursor", J. Chem. Soc., Perkin Trans. 1, 1999, 3357:3366.
Anderson et al., "Photophysical Characterization and Singles Oxygen Yield of a Dihydrofullerene", J. Am. Chem. Soc. 116:9763–9764, 1994.
Arimoto et al., "Multi–valent Polymer of Vancomycin: enhanced Antibacterial Activity Against VRE", Chem. Commun. 1361–1362, 1999.
Bergeron et al., "Water–Soluble Conducting Poly(aniline) Polymer", J. Chem. Soc., Chem. Commun. 180–182, 1990.
Corbell et al., "A comparison of Biological and Calorimetric Analyses of Multivalent Glycodendrimer Ligands for Concanavalen A", Tetrahedron: Asymmetry 11:95–111, 2000.
Fan et al., "High–affinity Pentavalent Ligands of Escherichia coli Heat–labile Enterotoxin by Modular Structure–based Design", J. Am. Chem. Soc. 122:2663–2664, 2000.
Fulton et al., "An Efficient Synthesis of Cyclodextrin–based Carbohydrate Cluster Compounds", Optical Letters 2:1113–1116, 2000.
Han et al., "Combination of Electrochemistry with Concurrent Reduction and Substitution Chemistry to Provide a Facile and Versatile Tool for Preparing Highly Functionalized Polyanilines", Chem. Mater. 11:480–486, 1999.
Han et al., "concurrent Reduction and Modification of Polyaniline Emeraldine Base with Pyrrolidine and Other Nucleophiles", Chem. Commun. 553–554, 1997.
Hany et al., "Polyanilines with Covalently Bonded Alkyl Sulfonates as Doping Agent, Synthesis and Properties", Synthetic Metals 31:369–378, 1989.
Irie et al., "Photocytotoxicity of Water–soluble Fullerene Derivatives", Biosci. Biotech. Biochem. 60:1359–1361, 1996.
Lamparth et al., "Reversible Template–Directed Activation of Equatorial Double Bonds of the Fullerene Framework: Regioselective Direct Synthesis, Crystal Structure, and Aromatic Properties of $T_h$–$C_{66}(COOEt)_{12}$", Agnew. Chem. Int. Ed. Engl. 34:1607–1609, 1995.

Lamparth et al., "Synthesis of [60]Fullerene Derivatives with an Octahedral Addition Pattern", Tetrahedron 52:5065–5075, 1996.
Lee et al., "Binding of Synthetic Oligosaccharides to the Hepatic Gal/GalNAc Lectin", The Journal of Biological Chemistry 258:199–202, 1983.
Lu et al., "Phenyl–capped Octaaniline (COA): An Excellent Model for Polyaniline", J. Am. Chem. Soc. 108:8311–8313, 1986.
Mammen et al., "Polyvalent Interactions in Biological Systems: Implications for Design and Use of Multivalent Ligands and Inhibitors", Angew. Chem. Int. Ed. 37:2754–2794, 1998.
Nakamura et al. "Biological Activity of Water–Soluble Fullerenes. Structural dependence of DNA Cleavage, Cytotoxicity, and Enzyme Inhibitory Activities Including HIV–Protease Inhibition", Bull. Chem. Soc. Jpn. 69:2143–2151, 1996.
Nguyen et al., "Synthesis and Properties of Novel Water–Soluble Conducting Polyaniline Copolymers", Macromolecules 27:3625–3631, 1994.
Nguyen et al., "Water–soluble Conductive–electroactive Polymers", Trip 3:186–190, 1995.
Rebourt et al., "Polyaniline Oligomers; Synthesis and Characterisation", Synthetic Metals 84:65–66, 1997.
Sadighi et al., "Palladium–catalyzed Synthesis of Monodiperse. Controlled–length. And Functionalized Oligoanilines", J. Am. Chem. Soc. 120:4960–4976, 1998.
Spaltenstein et al., "Polyacrylamides Bearing Pendant α–Sialoside Groups Strongly Inhibit Agglutination of Erthrocytes by Influenza Virus", J. Am. Chem. Soc. 113:686–687, 1991.
Tabata et al., "Photodynamic Effect of Polyethylene Glycol–modified Fullerene on Tumor", Jpn. J. Cancer Res. 88:1108–1116, 1997.
Wang et al., "Enhanced Inhibition of Human Anti–gal Antibody Binding to Mammalian Cells by Synthetic α–Gal Epitope Polymers", J. Am. Chem. Soc. 121:8174–8181, 1999.
Wei et al., "A New Synthesis of Aniline Oligomers with Three to Eight Amine Units", Aynthetic Metals 84:289–291, 1997.
Yue et al., "Effect of Sulfonic Acid Group on Polyaniline Backbone", J. Am. Chem. Soc. 113:2665–2671, 1991.
Yue, "Synthesis of Self–doped Conducting Polyaniline", J. Am. Chem. Soc. 112:2800–2801, 1990.
Zhang et al., "Synthesis of Oligomeric Anilines", Synthetic Metals 84:19–120, 1997.

* cited by examiner

Primary Examiner—Gary Geist
Assistant Examiner—Hector M Reyes
(74) Attorney, Agent, or Firm—Fish & Richardson P.C.

(57) ABSTRACT

A compound, of the following formula:

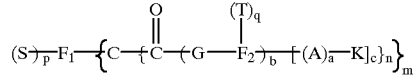

Also disclosed is a pharmaceutical composition containing a pharmaceutically effective amount of the compound.

33 Claims, No Drawings

MULTIOLIGONANILINATED FULLERENES

BACKGROUND OF THE INVENTION

Free radicals have been shown to inhibit tumor growth by causing oxidative damage to lipids, proteins, and nucleic acids of the tumor cells. In clinical practice, a photosensitizer is first delivered to a tumor site and then activated by irradiation to generate free radicals, thus inhibiting tumor growth. Among known photo-sensitizers, Photofrin II has recently been approved by the U.S. Food and Drug Administration. Preparation of Photofrin II is tedious.

Fullerenes are conjugated olefins of a closed cage structure. When photo-excited, they are capable of transforming molecular oxygen into singlet oxygen and then the related free radicals, such as superoxide free radicals, i.e., $O_2^-$. However, fullerenes have low bioavailability and must be chemically modified before they can be tested for their efficacy, if any, as photo-sensitizers in treating tumor.

SUMMARY OF THE INVENTION

One aspect of this invention relates to multioligoanilinated fullerenes (MOAFs) of the following formula:

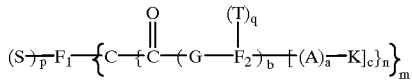

In this formula, p and each q, independently, is an integer of 0–20; each a is an integer of 1–8; each b is 0 or 1; each c is an integer of 1–20, provided that when b is 0, c is 1; each n is 1 or 2; m is an integer of 1–20; $F_1$ and each $F_2$, independently, is a $C_{60-66}$ or $C_{70-76}$ fullerene, preferably a $C_{60-66}$ or $C_{70}$ fullerene; each of S and T, independently, is —OH, —$NH_2$, —NHR, or —SH, wherein R is $C_{1-20}$ alkyl; each A, independently, is an oligoaniline, the term "oligoaniline" referring to a linear chemical species, the backbone of which consists of 2–12 aniline units; each nitrogen atom of the oligoaniline is optionally substituted with —Z, —$CH_2$—CO—OH, —$CH_2$—CO—O—Z, —$CH_2$—CO—S—Z, —$CH_2$—CO—$NH_2$, or —$CH_2$—CO—NH—Z; and each benzene ring is optionally substituted with —O—Z, —S—Z, —NH—Z; Z being —E—D, wherein E is —R—, —R—Ar—, —Ar—R—, or —Ar—; and D is —OH, —SH, —$NH_2$, —NHOH, —$SO_3H$, —$OSO_3H$, —$CO_2H$, —$CONH_2$, —CH—($NH_2$)—$CO_2H$, $P(OH)_3$, —$PO(OH)_2$, —O—$PO(OH)_2$, —O—PO(OH)—O—$PO(OH)_2$, —O—$PO(O^-)$—O—$CH_2CH_2NH_3^+$, -glycoside, —$OCH_3$, —$OCH_2(CHOH)_4$—$CH_2OH$, —$OCH_2(CHOH)_2$—$CH_2OH$, —$C_6H_3(OH)_2$, —$NH_3^+$, —$N^+H_2R_b$, —$N^+HR_bR_c$, or —$N^+R_bR_cR_d$, each of $R_b$, $R_c$, and $R_d$, independently, being $C_{1-20}$ alkyl; and Ar being aryl; each K, independently, is —H, —[N(X)—$C_6H_4]_{1-3}$—$NH_2$, —[N(X)—$C_6H_4]_{1-3}$—NH—C(=S)—SH, —[N(X)—$C_6H_4]_{1-3}$—N=CH—Ar—SH, —[N(X)—$C_6H_4]_{1-3}$—NH—CO—Ar—SH, wherein X is —H, —Z, —$CH_2$—CO—OH, —$CH_2$—CO—O—Z, —$CH_2$—CO—S—Z, —$CH_2$—CO—$NH_2$, —$CH_2$—CO—NH—Z; and Ar is aryl; each G, independently, is —O—B—R—O—, —NH—B—R—NH—, —O—B—R—NH—, —NH—B—R—O—, —O—B—R—S—, —NH—B—R—S—, wherein R is $C_{1-30}$ alkyl; B, independently, is —$R_1$—O—$[Si(CH_3)_2$—O—$]_{1-1000}$, $C_{1-2000}$ alkyl, $C_{6-40}$ aryl, $C_{7-60}$ alkylaryl, $C_{7-60}$ arylalkyl, $(C_{1-30}$ alkyl ether$)_{1-100}$, $(C_{6-40}$ aryl ether$)_{1-100}$, $(C_{7-60}$ alkylaryl ether$)_{1-100}$, $(C_{7-60}$ arylalkyl ether$)_{1-100}$, $(C_{1-30}$ alkyl thioether$)_{1-100}$, $(C_{6-40}$ aryl thioether$)_{1-100}$, $(C_{7-60}$ alkylaryl thioether$)_{1-100}$, $(C_{7-60}$ arylalkyl thioether$)_{1-100}$, $(C_{2-50}$ alkyl ester$)_{1-100}$, $(C_{7-60}$ aryl ester$)_{1-100}$, $(C_{8-70}$ alkylaryl ester$)_{1-100}$, $(C_{8-70}$ arylalkyl ester$)_{1-100}$, —$R_1$—CO—O—$(C_{1-30}$ alkyl ether$)_{1-100}$, —$R_1$—CO—O—$(C_{6-40}$ aryl ether$)_{1-100}$, —$R_1$—CO—O—$(C_{7-60}$ alkylaryl ether$)_{1-100}$, —$R_1$—CO—O—$(C_{7-60}$ arylalkyl ether$)_{1-100}$, $(C_{4-50}$ alkyl urethane$)_{1-100}$, $(C_{14-60}$ aryl urethane$)_{1-100}$, $(C_{10-80}$ alkylaryl urethane$)_{1-100}$, $(C_{10-80}$ arylalkyl urethane$)_{1-100}$, $(C_{5-50}$ alkyl urea$)_{1-100}$, $(C_{14-60}$ aryl urea$)_{1-100}$, $(C_{10-80}$ alkylaryl urea$)_{1-100}$, $(C_{10-80}$ arylalkyl urea$)_{1-100}$, $(C_{2-50}$ alkyl amide$)_{1-100}$, $(C_{7-60}$ aryl amide$)_{1-100}$, $(C_{8-70}$ alkylaryl amide$)_{1-100}$, $(C_{8-70}$ arylalkyl amide$)_{1-100}$, $(C_{3-30}$ alkyl anhydride$)_{1-100}$, $(C_{8-50}$ aryl anhydride$)_{1-100}$, $(C_{9-60}$ alkylaryl anhydride$)_{1-100}$, $(C_{9-60}$ arylalkyl anhydride$)_{1-100}$, $(C_{2-30}$ alkyl carbonate$)_{1-100}$, $(C_{7-50}$ aryl carbonate$)_{1-100}$, $(C_{8-60}$ alkylaryl carbonate$)_{1-100}$, $(C_{8-60}$ arylalkyl carbonate$)_{1-100}$, —$R_1$—O—CO—NH—($R_2$ or Ar—$R_2$—Ar)—NH—CO—O—$(C_{1-30}$ alkyl ether, $C_{6-40}$ aryl ether, $C_{7-60}$ alkylaryl ether, or $C_{7-60}$ arylalkyl ether$)_{1-100}$, —$R_1$—O—CO—NH—($R_2$ or Ar—$R_2$—Ar)—NH—CO—O—$(C_{2-50}$ alkyl ester, $C_{7-60}$ aryl ester, $C_{8-70}$ alkylaryl ester, or $C_{870}$ arylalkyl ester$)_{1-100}$, —$R_1$—O—CO—NH—($R_2$ or Ar—$R_2$—Ar)—NH—CO—O—$(C_{1-30}$ alkyl ether, $C_{6-40}$ aryl ether, $C_{7-60}$ alkylaryl ether, or $C_{7-60}$ arylalkyl ether$)_{1-100}$—CO-NH-($R_2$ or Ar—$R_2$—Ar)—NH—CO—O—, —$R_1$—O—CO—NH—($R_2$ or Ar—$R_2$—Ar)—NH—CO—O—$(C_{2-50}$ alkyl ester, $C_{7-60}$ arylaryl ester, $C_{8-70}$ alkylaryl ester, or $C_{8-70}$ arylalkyl ester$)_{1-100}$—$R_3$—O—CO—NH—($R_2$ or Ar—$R_2$—Ar)—NH—CO—O—, —$R_1$—NH—CO—NH—($R_2$ or Ar—$R_2$—Ar)—NH—CO—O—$(C_{1-30}$ alkyl ether, $C_{6-40}$ aryl ether, $C_{7-60}$ alkylaryl ether, or $C_{7-60}$ arylalkyl ether$)_{1-100}$, —$R_1$—NH—CO—NH—($R_2$ or Ar—$R_2$—Ar)—NH—CO—$(C_{2-50}$ alkyl ester, $C_{7-60}$ aryl ester, $C_{8-70}$ alkylaryl ester, or $C_{8-70}$ arylalkyl ester$)_{1-100}$, —$R_1$—NH—CO—NH—($R_2$ or Ar—$R_2$—Ar)—NH—CO—O— $(C_{1-30}$ alkyl ether, $C_{6-40}$ aryl ether, $C_{7-60}$ alkylaryl ether, or $C_{7-60}$ arylalkyl ether$)_{1-100}$—CO—NH—($R_2$ or Ar—$R_2$—Ar)—NH—CO—O—, —$R_1$—NH—CO—NH—($R_2$ or Ar—$R_2$—Ar)—NH—CO—O—$(C_{2-50}$ alkyl ester, $C_{7-60}$ aryl ester, $C_{8-70}$ alkylaryl ester, or $C_{8-70}$ arylalkyl ester$)_{1-100}$—$R_3$O—CO—NH—($R_2$ or Ar—$R_2$—Ar)—NH—CO—O—, —$R_1$—O—CO—NH—($R_2$ or Ar—$R_2$—Ar)—NH—CO—NH—($C_{2-50}$ alkyl amide, $C_{7-60}$ aryl amide, $C_{8-70}$ alkylaryl amide, or $C_{8-70}$ arylalkyl amide$)_{1-100}$, or —$R_1$—NH—CO—NH—($R_2$ or Ar—$R_2$—Ar)—NH—CO—NH—($C_{2-50}$ alkyl amide, $C_{7-60}$ aryl amide, $C_{8-70}$ alkylaryl amide, or $C_{8-70}$ arylalkyl amide)$_{1-100}$; wherein each of $R_1$, $R_2$, and $R_3$, independently, is $C_{1-30}$ alkyl; and Ar is aryl.

Also within the scope of this invention are pharmaceutically acceptable salts of the MOAFs described above. Such a salt can be formed between a negatively charged ionic group (e.g., sulfonate or carbonate) in an MOAF and a positively charged counterion (e.g., a sodium ion). Likewise, a positively charged ionic group (e.g., ammonium) in an MOAF can also form a salt with a negatively charged counterion (e.g., chloride).

One subset of the MOAFs of this invention are featured by that a is an integer of 3–6. Another subset of the MOAFs are featured by that b is 1, or b is 0 and c is 1. Still another subset of the MOAFs are featured by that n is 2. Yet stilled another subset of the MOAFs are featured by that A is tetraaniline, optionally substituted at nitrogen atoms with Z; E is —R— or —R—Ar—; and D is —OH, —SH, —$NH_2$, —NHOH, —$SO_3H$, —$OSO_3H$, —$CO_2H$, —$CONH_2$, —$P(OH)_3$, —$PO(OH)_2$, —O—$PO(OH)_2$, —O—PO(OH)—O—$PO(OH)_2$, or —$NH_3^+$.

Another aspect of this invention relates to a pharmaceutical composition which includes a pharmaceutically effective amount of an MOAF described above and a pharmaceutically acceptable carrier. Examples of such a carrier include water, colloidal silica oxide, magnesium sterate, and cellulose.

An MOAF of this invention can be used as a photodynamic therapeutic agent to inhibit growth, including causing death, of tumor cells in a tumor site. Accordingly, this invention also relates to use of an MOAF for the manufacture of a medicament for this application.

Details of several embodiments of this invention are set forth in the accompanying description below. Other features, objects, and advantages of this invention will be apparent from the description and from the claims.

DETAILED DESCRIPTION OF THE INVENTION

An MOAF of this invention can be synthesized by methods well known in the art. For instance, a fullerene can be first converted to a fullerene carboxylate by reacting it with a carboxylating agent such as diethyl bromomalonate. The fullerene carboxylate derivative is then oligoanilinated and, optionally, modified at the introduced oligoaniline moieties to generate ionic groups, e.g., alkylsulfonyl. Another suitable moiety, such as fullerene, can be introduced by further modifying one of the ionic groups. Each fullerene moiety can also be modified for introduction of hydrophilic groups, e.g., hydroxy, by reacting with dilute NaOH in the presence of a phase-transfer catalyst and aerated oxygen.

An effective amount of MOAF thus prepared can be formulated with a pharmaceutically acceptable carrier to form a pharmaceutical composition before being administered to a subject in need of tumor treatment. "An effective amount" refers to the amount of the MOAF which is required to confer therapeutic effect on the treated subject. The interrelationship of dosages for animals and humans (based on milligrams per square meter of body surface) is described by Freireich et al., Cancer Chemother. Rep. 1966, 50, 219. Body surface area may be approximately determined from height and weight of the patient. See, e.g., Scientific Tables, Geigy Pharmaceuticals, Ardley, N.Y., 1970, 537. Effective doses will also vary, as recognized by those skilled in the art, depending on the route of administration, the excipient usage, the distance of tumor from the skin surface, the source of the irradiation, and the optional co-usage with other therapeutic treatments including use of other anti-tumor compounds. Examples of pharmaceutically acceptable carriers include colloidal silicon dioxide, magnesium stearate, cellulose, sodium lauryl sulfate, and D&C Yellow #10.

The pharmaceutical composition may be administered via a parenteral route, e.g., topically, intraperitoneally, and intravenously. Examples of parenteral dosage forms include an active compound dissolved in phosphate buffer solution (PBS), or admixed with any other pharmaceutically acceptable carrier. Solubilizing agents, such as cyclodextrins, or other solubilizing agents well known to those familiar with the art, can also be included in the pharmaceutical composition.

The invention also relates to the use of an MOAF of this invention or a composition containing thereof for the manufacture of a medicament for tumor. More specifically, the MOAF is administered to the tumor site and the irradiated with laser or other light sources, e.g., fluorescence or X-ray. The irradiation can be of a wavelength of 400–1000 nm and an energy intensity of 10–300 J/cm$^2$, and the irradiation time can be 10–200 minutes. Upon irradiation, superoxide radicals are generated, which in turn attack and inhibit the growth of tumor cells.

An in vitro inhibition assay can be used to preliminarily evaluate an MOAF's ability to inhibit the growth of tumor cells. For example, an MOAF solution can be added to a pre-incubated cell suspension. Subsequently, the cell suspension is irradiated with fluorescence light, followed by further incubation. 3-(4,5-dimethylthiazol-2-yl)-2,5-diphenyl-tetrazolium bromide solution is then added to the cell suspension to react with mitochrondrial dehydrogenase to form formazon, which is extracted with dimethyl sulfoxide (DMSO). The DMSO extract solution is immediately used for optical measurement to determine the quantity of the formazon, which correlates with the quantity of dehydrogenase or the relative number of the living cells.

The MOAFs of this invention, which have been preliminarily evaluated, can be further screened for their efficacy by an in vivo inhibition assay using tumor-bearing mice. For example, each tumor-bearing mouse can be first administered with an MOAF to be tested in PBS close to the tumor site. The mouse is then kept in the dark while the MOAF is circulated to the tumor site. The tumor site is exposed by removing the hair on and around it and then irradiated with a laser beam or other light source. The growth of the tumor in the mouse is then examined at different time intervals. The inhibitory effect is evaluated by measuring the mouse's body weights and tumor volumes. After the mouse is sacrificed, the body weight and various organ weights are also measured, and blood samples are withdrawn for biochemistry and hematology analyses. All such data can be used to evaluate the efficacy of the MOAF to treat tumor.

Without further elaboration, it is believed that one skilled in the art, based on the description herein, can utilize the present invention to its fullest extent. All publications recited herein are hereby incorporated by reference in their entirety. The following specific examples, which describe synthesis and biological testing of several MOAFs of this invention, are therefore to be construed as merely illustrative, and not limitative of the remainder of the disclosure in any way whatsoever.

EXAMPLE 1

(1) Synthesis of diethylmalonate monoadduct of $C_{60}$ (F2E)

A mixture of $C_{60}$, diethyl bromomalonate (1.0 equiv.), 9,10-dimethylanthracene (DMA, 1.2 equiv.), and diazabicyclo[5.4.0]undec-7-ene (DBU, 1.2 equiv.) in toluene was used in an ethyl malonate-addition reaction on $C_{60}$ at ambient temperature for 10 hours. See Hirsch et al. *J. Am. Chem. Soc.*, 1994, 116, 9385. The product mixture thus obtained was subjected to repeated $SiO_2$ chromatographic separation by using toluene-hexane (1:2) as the eluent. One thin layer chromatography (TLC, $R_f$ 0.75) fraction, corresponding to the product, $C_{60}$-[C(CO$_2$Et)$_2$], were isolated in a 54% yield.

m/z (relative intensity, %): 879 (n=1), and 720 ($C_{60}$).

IR (KBr) vmax: 3392 (br), 2930 (C—H), 2859, 1656, 1596, 1504 (s), 1316, 1170, 1115, 835, 751, 697, and 508 cm$^{-1}$.

$^1$H-NMR δ: 6.50–7.30 (m).

(2) Synthesis of dodecaethylhexakis(methano)[60] fullerene dodecacarboxylate (F12E) and decaethylpentakis(methano)[60]fullerene decacarboxylate (F10E)

A mixture of $C_{60}$, diethyl bromomalonate (6.0 equiv.), 9,10-dimethoxyanthracene (DMOA, 10 equiv.), and DBU (7.0 equiv.) in toluene was stirred at ambient temperature for 12 hours. Into the reaction flask, additional diethyl bromomalonate (4.0 equiv.) and DBU (5.0 equiv.) were charged. The reaction was allowed to continue for 24 hours. See Hirsch et al. *Angew. Chem. Int. Ed. Engl.* 1995, 34, 1607. The product mixture thus obtained was subjected to repeated $SiO_2$ chromatographic separation by using THF-toluene (1:9) as the eluent. Three thin layer chromatography (TLC) fractions, corresponding to there products, $C_{60}$-$[C(CO_2Et)_2]_n$ (n=3, 4, and 5, respectively), were isolated and identified by their molecular ion mass as $C_{60}$-malonate adducts: F8E (n=4, $R_f$ 0.62, m/z 1353, 7.5% yield), F10E (n=5, $R_f$ 0.53, m/z 1511, 21% yield), and F12E (n=6, $R_f$ 0.44, m/z 1669, 56% yield).

F8E m/z (relative intensity, %): 1353 (100, n=4), 1195 (9.9, n=3), 1037 (5.7, n=2), and 720 (38.8).

IR (KBr) $v_{max}$: 3441 (br), 2983 (C—H), 2938, 2907, 2874, 1747 (s, ester carbonyl), 1465, 1446, 1391, 1369, 1299, 1235 (s), 1180 (shoulder), 1108, 1065, 1023, 861, 815, 737, 708, and 528 $cm^{-1}$.

UV-Vis ($1.0 \times 10^{-5}$ M in THF) $\lambda_{max}$: 294 and 469 nm.

F10E m/z (relative intensity, %): 1511 (100, n=5), 1353 (16.9, n=4), 1195 (13.7, n=3) 1037 (11.2, n=2), 878 (8.1, n=1), and 720 (44.7).

IR (KBr) vmax: 3454 (br), 2983 (C—H), 2939, 2908, 2875, 1747 (s, ester carbonyl), 1466, 1447, 1392, 1370, 1297, 1233 (s), 1179 (shoulder), 1112, 1098, 1073, 1023, 859, 817, 737, 708, and 525 $cm^{-1}$.

UV-Vis (THF, $1.0 \times 10^{-5}$ M) $\lambda_{max}$: 286 and 444 nm.

$^{13}C$ NMR ($CDCl_3$, major brown-red regioisomer) δ: 41.5, 43.7, 46.8, 47.2, 48.9, 49.8, 67.5, 68.5 (2C), 68.9, 69.3, 69.5, 69.6, 70.6, 70.9, 71.2, 72.1, 134.0, 135.1, 136.9, 137.8, 138.1, 139.2, 139.4, 139.7, 139.8, 140.5, 140.6, 140.7, 140.8, 140.9, 141.24, 141.23, 141.3, 141.4, 141.8, 141.9, 142.0, 142.1, 142.6, 142.9, 143.0, 143.6, 143.7, 143.8, 144.0, 144.2, 144.3, 144.36, 144.39 (2C), 144.7, 144.8, 145.2, 145.4, 145.4, 145.6, 145.8, 145.1, 146.2, 146.9, 147.2, 147.4, 147.6, 147.7, and 147.8 (2C).

F12E m/z (relative intensity, %): 1669 (100, n=6), 1511 (15.5, n=5), 1353 (10.9, n=4) 1195 (8.8, n=3), 1037 (4.3, n=2), 879 (4.6, n=1), and 720 (53.7);

IR (KBr) $v_{max}$: 3455 (br), 2985, 2939 (C—H), 2910, 2875, 1747 (s, ester carbonyl), 1467, 1448, 1393, 1370, 1297, 1241 (s), 1223 (s), 1177 (shoulder), 1096, 1080, 1020, 859, 815, 715, and 527 $cm^{-1}$.

UV-Vis ($1.0 \times 10^{-5}$ M in THF) $\lambda_{max}$: 278 and 337 nm.

$^1$H-NMR δ: 1.17–1.34 (m, 36H), 4.31–4.41 (m, 24H).

$^{13}C$ NMR ($CDCl_3$, yellow regioisomer) δ: 45.3, 69.0, 141.1, 145.7, and 163.8.

$^{13}C$ NMR ($CDCl_3$, orange-red regioisomer) δ: 64.2, 66.5, 66.9, 68.2, 68.3, 68.4, 68.8, 69.5, 69.8, 70.0, 70.4, 70.7, 130.9, 132.6, 134.7, 135.6, 137.2, 137.8, 138.1, 138.7, 139.2, 139.4, 139.7, 139.8, 140.2, 140.9, 141.3, 141.4, 141.6, 141.9 (4C), 142.0 (2C), 142.1, 142.2, 142.4, 142.5, 142.7, 143.9, 144.2, 144.4, 144.5, 144.8, 145.0, 145.2 (2C), 145.5 (2C), 145.6 (2C), 145.6 (3C), 145.9, 146.0, 146.1, 146.4, 147.7, 161.3, 162.9, 163.1, 163.2, 163.4, 163.64, 163.65, 163.7, 163.85 (2C), 163.9, and 164.0.

(3) Synthesis of fullerene bis(hexadecaaniline) adduct ($F2A_{16}$)

180 mg F2E (0.2 mmol) in 10.0 mL DMSO and 0.5 mL THF were mixed in a dry flask equipped with a stirring bar and a condenser under $N_2$. To the solution were then sequentially added 0.6 mL DBU (4.0 mmol), and 660 mg hexadecaaniline ($A_{16}$) in the emeraldine base form (0.45 mmol) in 5.0 mL DMSO. The mixture thus obtained was stirred at 85–90° C. for 15.0 hours and then quenched with 100 mL water, which resulted in a solid precipitate. The precipitate, which included $F2A_{16}$ and impurities, was collected after centrifugation, washed twice with acetonitrile, and dissolved in 10 mL DMSO. The DMSO solution was then slowly added to 100 mL acetonitrile. The product, $F2A_{16}$, in the form of a precipitate, was collected after centrifugation and then purified by $SiO_2$ TLC until no hexadecaaniline [$R_f$0.7–0.75, THF—$CHCl_3$ (1:1)-pyridine (one drop)] was detectable. The resulting blue solids were then dried under vacuum at 40° C. to give 590 mg $F2A_{16}$ in an 80% yield.

$F2A_{16}$

IR (KBr) $v_{max}$: 3388 (br), 3035, 2933 (C—H), 2860, 1656 (amide), 1600, 1506 (s), 1300, 1172, 1123, 1044, 829, 751, 698, and 508 $cm^{-1}$.

UV-Vis ($1.5 \times 10^{-6}$ M in DMSO) $\lambda_{max}$: 325 (benzenoid absorption) and 595 (quinonoid absorption) nm.

$^1$H-NMR δ: 6.67 (m, 17H), 6.90 (m, 86H), 7.11 (m, 25H), and 7.75 (N—H, 8H, disappear in $D_2O$).

(4) Synthesis of fullerene deca(hexadecaaniline) ($F10A_{16}$) and dodeca(hexadecaaniline) ($F12A_{16}$) adducts $F10A_{16}$ and $F12A_{16}$ were prepared by the method as described in step (3) above, except that F10A and F12A were respectively used instead of F2A. The yields were 70–78%.

$F10A_{16}$

IR (KBr) vmax: 3382 (br), 3280 (br), 3036, 2936 (C—H), 2865, 1648 (amide), 1600, 1504 (s), 1300, 1174, 1116, 828, 751, 697, 619, and 509 $cm^{-1}$.

UV-Vis ($1.0 \times 10^{-6}$ M in DMSO) $\lambda_{max}$: 325 and 595 nm.

$^1$H-NMR δ: 6.67 (m, 8H), 6.90 (m, 44H), 7.11 (m, 12H), and 7.6–7.8 (N—H, 4H, disappeared in $D_2O$).

$F12A_{16}$

IR (KBr) $v_{max}$: 3387 (br), 3033 (br), 2931 (C—H), 2859, 1659 (amide), 1599, 1505 (s), 1298, 1171, 1128, 826, 750, 697, 636, and 507 $cm^{-1}$.

UV-Vis ($1.0 \times 10^{-6}$ M in DMSO) $\lambda_{max}$: 323 (benzenoid absorption) and 595 (quinonoid absorption) nm.

$^1$H-NMR δ: 6.67 (m, 8H), 6.94 (m, 44H), 7.11 (m, 12H), and 7.7–7.9 (N—H, 4H, disappear in $D_2O$).

EXAMPLE 2

Synthesis of sulfobutylated fullerene dodeca (hexadecaanilino)adduct ($F12A_{16}S$), deca (hexadecaanilino)adduct ($F10A_{16}S$), and di (hexadecaanilino)adduct ($F2A_{16}S$)

200 mg $F12A_{16}$ and 15.0 mL DMF were added to a dry flask containing a stirring bar and a condenser under $N_2$. To the DMF solution were either sequentially added 1.0 mL DBU, 0.5 mL 1,4-butane sultone, and stirred at 100° C. for 12.0 hours or sequentially added 70 mg sodium hydride −30° C., stirred for 30 minutes, added 0.5 mL 1,4-butane sultone, and stirred at 60° C. for 6.0 hours. It was then quenched with 100 mL dilute HCl-acetone solution to effect precipitation of a solid. The solid was collected after centrifugation, washed twice with acetonitrile, and dissolved in 15 mL DMSO-$H_2O$ (1:5) in the presence of 100 mg $Na_2CO_3$. The DMSO-$H_2O$ solution was slowly added to acetone, resulting in precipitation of the product $F12A_{16}S$. The product, in blue, was collected after centrifugation, washed with DMF and acetone, and then dried under vacuum at 40° C. to yield 210–230 mg water-soluble $F12A_{16}S$.

F12A$_{16}$S

IR (KBr) $v_{max}$: 3445 (br), 2944 (C—H), 2873, 1625 (amide, s), 1523, 1504, 1451, 1330, 1199 (s), 1044, 825, 729, 609, and 530 cm$^{-1}$.

UV-Vis (2.0×10$^{-6}$ M in H$_2$O) $\lambda_{max}$: 328 (benzenoid absorption) and 605 (quinonoid absorption) nm.

$^1$H-NMR (D$_2$O) δ: 1.70 (m, 4H), 2.88 (t, 2H), 3.57 (t, 2H), and 7.0–7.8 (aromatic).

F2A$_{16}$S and F10A$_{16}$S were prepared by the same method as described above, except that F2A$_{16}$ and F10A$_{16}$ were respectively used.

F2A$_{16}$S

IR (KBr) $v_{max}$: 3442 (br), 2938 (C—H), 2873, 1622 (amide), 1605, 1506, 1417 (w), 1360 (w), 1183 (s), 1046, 827, 609, and 526 cm$^{-1}$.

F10A$_{16}$S

IR (KBr) $v_{max}$: 3427 (br), 2928 (C—H), 2859, 1647 (amide), 1598, 1503, 1317, 1171, 1039, 806, 606, and 518 cm$^{-1}$.

$^1$H-NMR δ(D$_2$O): 1.3–1.9 (4H), 2.7–2.9 (2H), 3.4–3.6 (2H), and 6.4–7.2 (aromatic).

EXAMPLE 3

(1) Synthesis of F10A$_4$

F10A$_4$ was prepared by the method described in Example 1 (3), except that F10E and tetraaniline (A$_4$) in the emeraldine base form were used instead of F2E and A$_{16}$.

IR (KBr) $v_{max}$: 3388 (br), 3030 (C—H), 2942 (C—H), 2810, 1601 (amide), 1506 (s), 1293, 1255, 1170, 820, 750, 696, and 506 cm$^{-1}$.

(2) Synthesis of sulfobutylated deca(tetraanilino)-pentakis(methano)-[60]fullerene decacarbamide (F10A$_4$S)

80 mg F10A$_4$ in 20 mL DMSO, and 60 mg sodium hydride were added into a dry flask equipped with a stirring bar and a condenser at ambient temperature under N$_2$. The solution thus obtained was stirred for 30 minutes, followed by addition of 0.2 mL 1,4-butane sultone. The reaction mixture was slowly heated to 70° C. and stirred for 12.0 hours, and was quenched with 100 mL dilute HCl-acetonitrile solution to effect precipitation. The precipitate was collected after centrifugation, washed twice with acetonitrile, and dissolved in 10 mL H$_2$O. The aqueous solution was then filtered through a celite filtering agent, and dried, to produce a blue precipitate. The blue precipitate was washed again with acetonitrile and dried under vacuum at 40° C. to give 95 mg water-soluble F10A$_4$S.

IR (KBr) vmax: 3460 (br), 2945 (C—H), 2874, 1653 (amide, s), 1509, 1419 (w), 1186 (s), 1048 (s), 795, 611, and 533 cm$^{-1}$.

$^1$H-NMR δ(D$_2$O): 1.2–1.9 (4H), 2.65–2.85 (2H), 3.2–3.5 (2H), and 6.3–7.0 (aromatic).

EXAMPLE 4

In vitro Irradiation-induced Superoxide Generation by F10A$_4$S

F10A$_4$S's ability to generate superoxide free radicals was demonstrated as follows: 1.0 mL 25 μM F10A$_4$S aqueous solution was added to 1.0 mL ferricytochrome C-containing PBS (50 μM). The solution thus obtained was added to each well of a 24-well plate, and exposed to fluorescence light source (27 watts) for 0–90 min. The distance between the plate cover and the light source was set at 5–6 cm. The extent of reduction of ferricytochrome C to ferrocytochrome C was evaluated by optical measurement. The increase of the absorbance at 550 nm corresponded to the increase of the quantity of ferrocytochrome C. Production of ferrocytochrome C indicated that F10A$_4$S, upon irradiation, converted molecular oxygen by subsequent reactions to superoxide free radicals, and electron transfer from the superoxide free radicals to ferricytochrome C reduced the ferricytochrome C to ferrocytochrome C. The production of superoxide radicals was observed to increase systematically in a time-dependent manner with the irradiation time increasing from 0, 30, 60, to 90 minutes at a constant F10A$_4$S concentration of 25 μM.

In a separate experiment, the presence of superoxide radicals in the solution was confirmed by selective removal of superoxide radicals with superoxide dismutase (SOD, 75 or 150 units). SOD effectively suppressed the irradiation-induced generation of superoxide radicals by F10A$_4$S at 25 μM for 90 minutes. The data confirm a linear correlation between the optical absorbance at 550 nm and the quantity of superoxide radicals produced by irradiation of F10A$_4$S in the presence of molecular oxygen.

EXAMPLE 5

In vitro Irradiation-induced Cytotoxicity of F10A$_{16}$S Based on Tumor Cell Viability Two types of tumor cells were used in this study, and prepared as follows: Fibrosarcoma cells (CCRC 60037) and sarcoma 180 cells (obtained form Biochemical Institute of Chung Shan Medical and Dental College, Taiwan) were maintained and cultured in an α-modified eagle medium (MEM) containing L-glutamine and phenol red. It was supplemented with 10% fetal bovine serum and antibiotics (100 units/mL of penicillin G and 100 μg/mL streptomycin sulfate). The cells were incubated in the dark in 95% humidified air plus 5% CO$_2$, and harvested by treatment with trypsin-EDTA. The harvested cells were suspended in an α-MEM medium at the concentration of 1×10$^4$ cells per mL.

The cell suspension thus obtained was placed into wells of a 24-well plate (500 μL each) and pre-incubated at 37° C. for 24 hours. F10A$_{16}$S solutions at various concentrations (0–10 μM) were then added to the wells (500 μL each). The wells were irradiated with fluorescence light (27 watts) for 0–60 minutes. The distance between the plate cover and the light source was set at 5–6 cm. After irradiation, the cells were further incubated for 48 hours. A solution of 3-(4,5-dimethylthiazol-2-yl)-2,5-diphenyl-tetrazolium bromide (MTT, 100 μL, 0.5% in PBS, 100 μL each) was then added to each of the wells to react with mitochrondrial dehydrogenase in the living cells to produce formazon. Each cell suspension was again incubated at 37° C. for 3 hours. The suspension medium was then discarded. Formazon formed in cells from each well was then extracted with DMSO (1.0 mL each). The DMSO extract solution was immediately used for optical measurement. The absorbance at 540 nm was correlated with the quantity of formazon, and thus with the quantity of dehydrogenase enzyme or the relative number of living cells (i.e., viability). The results show a decrease in cell viability in both dose-dependent and irradiation time-dependent manners. With an irradiation time of 60 minutes, a sharp loss of viable cells was observed when F10A$_{16}$S concentration was increased from 2.5 to 5.0 μM. A maximal photodynamic cytotoxicity efficacy of >90% was obtained at an F10A$_{16}$S concentration of 5.0–10.0 μM and an irradiaion time of 60 minutes. IN the absence of light irradiation, no cystoxicity was observed even at the highest F10A$_{16}$S concentration, i.e., 10 μM. An IC$_{50}$ of F10A$_{16}$S of 2.9 μM was observed in irradiation treatment of the fibrosarcoma cells with an irradiation time of 60 minutes.

EXAMPLE 6

In vivo Photodynamic Therapy Study of F10A$_{16}$S

A photodynamic therapy study was conducted in male ICR mice (Charles River Japan origin Crl: CD-1® (ICR) BR). The mice were 8 weeks old, weighted 37±0.8 g, housed in polycarbonated shoe-box cages on hardwood bedding (5 mice/cage) under controlled conditions (temperature 22±1° C., relative humidity 55±15%, and light/dark cycle 12/12 hours), and allowed free access to a laboratory rodent diet (#5K55, Purina Mills, Inc., St. Louis, Mo.) and water.

Murine sarcoma 180 cells were maintained by transplantation to other mice in the abdominal cavity biweekly. Subcutaneous tumors were induced by intraperitoneal injection of 1×10$^7$ tumor cells (about 0.1–0.15 ml ascitic fluid) to the subcutaneous region of abdominal cavities of the mice for this study, and were allowed to proliferate at the inoculation sites for 5–7 days until they reached a size with a diameter of 10±2 mm. Thirty tumor-bearing mice were divided into 3 groups, including (a) tumor control, (b) intraperitoneal injection of F10A$_{16}$S (10 mg/kg) to tumor-bearing mice followed by laser irradiation oat 514 nm, and (c) intraperitoneal injection to F10A$_{16}$S (10 mg/kg) on tumor-bearing mice followed by laser irradiation at 633 nm.

Each mouse in groups (b) and (c) was intraperitoneally injected with F10A$_{16}$S in PBS at a site roughly 2.0 cm away from the tumor location, kept in the dark for 24 hours to allow bio-distribution of F10A$_{16}$S to the tumor site, and then anesthetized by avertine (0.3 mL/head). The tumor site in each mouse in groups (b) and (c) was exposed by removing the hair on and around it, and then subsequently irradiated with an argon ion laser beam (Spectra Physics, Model 168) at a wavelength of 514 or 633 nm. The beam was delivered via a quartz fiber with the circular area of illumination output focused to a diameter of 7–8 mm with the total light dose adjusted to a level of 100 J/cm$^2$ in each experiment.

After the treatment, the mouse was examined every 5 days for 30 days. Efficacy of the irradiation therapy was evaluated by measuring the body weights and tumor volumes of the mouse. At day 30, the mice were euthanatized by carbon dioxide asphyxiation, and the weights of the body, liver, kidney, spleen, heart, and tumor, were measured. Blood samples were withdrawn, and plasma biochemistry and blood hematology analyses were conducted with a Hitachi 7050 Automatic Analyzer and a Serono System 9000, respectively.

All of the irradiation-treated mice showed sharp decreases in the weights of the isolated tumors. At the F10A$_{16}$S concentration of 10 mg/kg, the tumor weight in the mice of group (b), i.e., irradiated at 514 nm, reached roughly 60% less than that of the tumor control group. At the same F10A$_{16}$S concentration, the tumor weight in the mice of group (c), i.e., irradiated at 633 nm, was nearly 99% less than that of the tumor control group. These results indicated an unexpectedly high efficacy of F10A16S on reducing the viability and proliferation of fibrosarcoma tumor cells in photodynamic therapy.

OTHER EMBODIMENTS

A number of embodiments of the invention have been described. Nevertheless, it will be understood that various modifications may be made without departing from the spirit and scope of the invention. For example, the oligoanilinated fullerenes can be used as photoactivated biocidal agents, or drugs capable of forming multi-covalent bonds with a target. Accordingly, other embodiments are within the scope of the following claims.

What is claimed is:

1. A compound of the following formula:

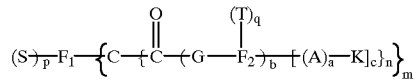

wherein p and each q, independently, is an integer of 0–20;

each a is an integer of 1–8;

each b is 0 or 1;

each c is an integer of 1–20, provided that when b is 0, c is 1, each n is 1 or 2;

m is an integer of 1–20;

F$_1$ and each F$_2$, indepedently, is a fullerene;

each of S and T, independently, is —OH, —NH$_2$, —NHR, or —SH, wherein R being C$_{1-30}$ alkyl;

each A, independently, is an oligoaniline, wherein each nitrogen atom is optionally substituted with —Z, —CH$_2$—CO—OH, —CH$_2$—CO—O—Z, —CH$_2$—CO—S—Z, —CH$_2$—CO—NH$_2$, or —CH$_2$—CO—NH—Z; each benzene ring is optionally substituted with —O—Z, —S—Z, —NH—Z; Z being —E—D, wherein E is —R—, —R—Ar—, —Ar—R—, or —Ar—; and D is —OH, —SH, —NH$_2$, —NHOH, —SO$_3$H, —OSO$_3$H, —CO$_2$H, —CONH$_2$, —CH—(NH$_2$)—CO$_2$H, —P(OH)$_3$, —PO(OH)$_2$, —O—PO (OH)$_2$, —O—PO(OH)—O—PO(OH)$_2$, —O—PO (O$^-$)—O—CH$_2$CH$_2$NH$_3$$^+$, -glycoside, —OCH$_3$, —OCH$_2$(CHOH)$_4$—CH$_2$OH, —OCH$_2$(CHOH)$_2$—CH$_2$OH, —C$_6$H$_3$(OH)$_2$, —NH$_3$$^+$, —N$^{30}$ H$_2$R$_b$, —N$^+$HR$_b$R$_c$, or —N$^+$R$_b$R$_c$R$_d$, R being C$_{1-30}$ alkyl; each of R$_b$, R$_c$, and R$_d$, independently, being C$_{1-20}$ alkyl; and Ar being aryl;

each K, independently, is —H$_3$—[N(X)—C$_6$H$_4$]$_{1-3}$—NH$_2$, —[N(X)—C$_6$H$_4$]$_{1-3}$—NH—C(═S)—SH, —[N(X)—C$_6$H$_4$]$_{1-3}$—N═CH—Ar—SH, —[N(X)—C$_6$H$_4$]$_{1-3}$—NH—CO—Ar—SH, wherein X is —H, —Z, —CH$_2$—CO—OH, —CH$_2$—CO—O—Z, —CH$_2$—CO—S—Z, —CH$_2$—CO—NH$_2$, —CH$_2$—CO—NH—Z; and Ar is aryl;

each G, independently, is —O—B—R—O—, —NH—B—R—NH—, —O—B—R—NH—, —NH—B—R—O—, —O—B—R—S—, —NH—B—R—S—, wherein R is C$_{1-30}$alkyl; B, independently, is —R$_1$—O—[Si(CH$_3$)$_2$—O—]$_{1-100}$, C$_{1-2000}$ alkyl, C$_{6-40}$ aryl, C$_{7-60}$ alkylaryl, C$_{7-60}$ arylalkyl, (C$_{1-30}$ alkyl ether)$_{1-100}$ (C$_{6-40}$ aryl ether)$_{1-100}$, (C$_{7-60}$ alkylaryl ether)$_{1-100}$, (C$_{7-60}$ alalkyl ether)$_{1-100}$, (C$_{1-30}$ alkyl tioether)$_{1-100}$, (C$_{6-40}$ aryl thioether)$_{1-100}$, (C$_{7-60}$ alkylaryl thioether)$_{1-100}$, (C$_{7-60}$ arylalkyl thioether)$_{1-100}$, (C$_{2-50}$ alkyl ester)$_{1-100}$, (C$_{7-60}$ aryl ester)$_{1-100}$, (C$_{K-70}$ alkylaryl ester)$_{1-100}$, (C$_{8-70}$ arylalkyl ester)$_{1-100}$, —R$_1$—CO—O—(C$_{1-30}$ alkyl ether)$_{1-100}$, —R$_1$—CO—O—(C$_{6-40}$ aryl ether)$_{1-100}$, —R$_1$—CO—O—(C$_{7-60}$ alkylaryl ether)$_{1-100}$, —R$_1$—CO—O—(C$_{7-60}$ arylalkyl ether)$_{1-100}$, (C$_{4-50}$ alkyl urethane)$_{1-100}$, (C$_{14-60}$ aryl urethane)$_{1-100}$, (C$_{10-80}$ alkylaryl urethane)$_{1-100}$, (C$_{10-80}$ arylalkyl urethane)$_{1-100}$, (C$_{5-50}$ alkyl urea)$_{1-100}$, (C$_{14-60}$ aryl urea)$_{1-100}$, (C$_{10-80}$ alkylaryl urea)$_{1-100}$, (C$_{10-80}$ arylalkyl urea)$_{1-100}$, C$_{2-50}$ alkyl amide)$_{1-100}$, (C$_{7-60}$ aryl amide)$_{1-100}$, (C$_{8-70}$ alkylaryl amide)$_{1-100}$, (C$_{8-70}$ arylalkyl amide)$_{1-100}$, (C$_{3-30}$ alkyl anhydride)$_{1-100}$, (C$_{8-50}$ aryl anhydride)$_{1-100}$, (C$_{9-60}$ alkylaryl anhydride)$_{1-100}$, (C$_{9-60}$ arylalkyl anhydride)$_{1-100}$, (C$_{2-30}$ alkyl carbonate)$_{1-100}$, (C$_{7-50}$ aryl carbonate)$_{1-100}$, (C$_{8-60}$ alkylaryl carbonate)$_{1-100}$, (C$_{8-60}$ arylalkyl carbonate)$_{1-100}$, —R$_1$—O—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$, —R$_1$—O—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$, —R$_1$—O—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$, —CO—NH—(R$_2$ or Ar—R$_2$—Ar)—NH—CO—O—, —R$_1$—O—CO—NH—(R$_2$ or Ar—R$_2$—Ar)—NH—CO—O—(C$_{2-50}$ alkyl ester, C$_{7-60}$ aryl ester, C$_{8-70}$ alkylaryl ester, or C$_{8-70}$ arylalkyl ester)$_{1-100}$—R$_3$—O—CO—NH—(R$_2$ or Ar—R$_2$—Ar)—NH—CO—O—, —R$_1$—NH—CO—NH—(R$_2$ or Ar—R$_2$—Ar)—NH—CO—O—(C$_{1-30}$ alkyl ether, C$_{6-40}$ aryl ether, C$_{7-60}$ alkylaryl ether, or C$_{7-60}$ arylalkyl ether)$_{1-100}$, —R$_1$—NH—CO—NH—(R$_2$ or Ar—R$_2$—Ar)—NH—CO—(C$_{2-50}$ alkyl ester, C$_{7-60}$ aryl ester, C$_{8-70}$ alkylaryl ester, or C$_{8-70}$ arylalkyl ester)$_{1-100}$, —R$_1$—NH—CO—NH—(R$_2$ or Ar—R$_2$—Ar)—NH—CO—O—(C$_{1-30}$ alkyl ether, C$_{6-40}$ aryl ether, C$_7$60 alkylaryl ether, or C$_{7-60}$ arylalkyl ether)$_{1-100}$—CO—NH—(R$_2$ or Ar—R$_2$—Ar)—NH—CO—O—, —R$_1$—NH—CO—NH—(R$_2$ or Ar—R$_2$—Ar)—NH—CO—O—(C$_{2-50}$ allyl ester, C$_{7-60}$aryl ester, C$_{8-70}$alkylaryl ester, or C$_{8-70}$ arylalkyl ester)$_{1-100}$—R$_3$O—CO—NH—(R$_2$ or Ar—R$_2$—Ar)—NH—CO—O—, —R$_1$—O—CO—NH—(R$_2$ or Ar—R$_2$—Ar)—NH—CO—NH—(C$_{2-50}$ alkyl amide, C$_{7-60}$ aryl amide, C$_{8-70}$ alkylaryl amide, or C$_{8-70}$ arylalkyl amide)$_{1-100}$, or —R$_1$—NH—CO—NH—(R$_2$ or Ar—R$_2$—Ar)—NH—CO—NH—(C$_{2-50}$ alkyl amide, C$_{7-60}$ aryl amide, C$_{8-70}$ alkylaryl amide, or C$_{8-70}$ arylalkyl amide)$_{1-100}$; wherein each of R$_1$, R$_2$and R$_3$, independently, is C$_{1-30}$ alkyl; and Ar is aryl.

2. The compound of claim 1, wherein a is an integer of 2–6.

3. The compound of claim 1, wherein b is 0; and c is 1.

4. The compound of claim 1, wherein n is 2.

5. The compound of claim 2, wherein b is 0; and c is 1.

6. The compound of claim 2, wherein a is 4.

7. The compound of claim 2, wherein n is 2.

8. The compound of claim 6, wherein b is 0; and c is 1.

9. The compound of claim 6, wherein n is 2.

10. The compound of claim 8, wherein n is 2.

11. The compound of claim 3, wherein n is 2.

12. The compound of claim 1, wherein A is tetraaniline, optionally substituted at one or more nitrogen atoms with Z; E is —R— or —R—Ar—; and D is —OH, —SH, —NH$_2$, —NHOH, —SO$_3$H, —OSO$_3$H, —CO$_2$H, —CONH$_2$, —P(OH)$_3$, —PO(OH)$_2$, —O—PO(OH)$_2$, —O—PO(OH)—O—PO(OH)$_2$, or —NH$_3^+$; Z, R, and Ar are defined in claim 1.

13. The compound of claim 12, wherein A is tetraaniline of the emeradine base form, substituted at the nitrogen atoms of the benzenoid units with —C$_3$H$_6$SO$_3$Na or —C$_4$H$_8$SO$_3$Na.

14. The compound of claim 12, wherein a is an integer of 2–6.

15. The compound of claim 12, wherein b is 0; and c is 1.

16. The compound of claim 12, wherein n is 2.

17. The compound of claim 13, wherein a is an integer of 2–6.

18. The compound of claim 13, wherein b is 0; and c is 1.

19. The compound of claim 13, wherein n is 2.

20. The compound of claim 17, wherein a is 4.

21. The compound of claim 20, wherein b is 0; c is 1; and n is 2.

22. The compound of claim 21, wherein m is an integer of 1–8.

23. The compound of claim 22, wherein F$_1$ is C$_{60}$ fullerene; K is H; and p is 0.

24. The compound of claim 18, wherein n is 2.

25. The compound of claim 14, wherein b is 0; and c is 1.

26. The compound of claim 14, wherein n is 2.

27. The compound of claim 15, wherein n is 2.

28. The compound of claim 1, wherein b is 1.

29. A pharmaceutical composition, comprising a compound of the following formula:

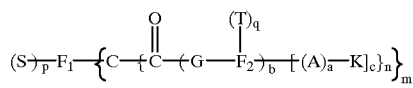

wherein
p and each q, independently, is an integer of 0–20;
each a is an integer of 1–8;
each b is 0 or 1;
each c is an integer of 1–20, provided that when b is 0, c is 1;
each n is 1 or 2;
m is an integer of 1–20;
F$_1$ and each F$_2$, independently, is a fullerene;
each of S and T, independently, is —OH, —NH$_2$, —NHR, or —SH, wherein R being C$_{1-30}$ alkyl;
each A, independently, is an oligoaniline, wherein each nitrogen atom is optionally substituted with —Z, —CH$_2$—CO—OH, —CH$_2$—CO—O—Z, —CH$_2$—CO—S—Z, —CH$_2$—CO—NH$_2$, or —CH$_2$—CO—NH—Z; each benzene ring is optionally substituted with —O—Z, —S—Z, —NH—Z; Z being —E—D, wherein E is —R—, —R—Ar—, —Ar—R—, or —Ar—; and D is —OH, —SH, —NH$_2$, —NHOH, —SO$_3$H, —OSO$_3$H, —CO$_2$H, —CONH$_2$, —CH—(NH$_2$)—CO$_2$H, —P(OH)$_3$, —PO(OH)$_2$, —O—PO(OH)$_2$, —O—PO(OH)—O—PO(OH)$_2$, —O—PO(O$^-$)—O—CH$_2$CH$_2$NH$_3^+$, -glycoside, —OCH$_3$, —OCH$_2$(CHOH)$_4$—CH$_2$OH, —OCH$_2$(CHOH)$_2$—CH$_2$OH, —C$_6$H$_3$(OH)$_2$, —NH$_3^+$, —N$^+$H$_2$R$_b$, N$^+$HR$_b$R$_c$or —N$^+$R$_b$R$_c$R$_d$, R being C$_{1-30}$ alkyl; each of R$_b$, R$_c$, and R$_d$, independently, being C$_{1-20}$ alkyl; and Ar being aryl;

each K, independently, is —H, —[N(X)—C$_6$H$_4$]$_{1-3}$—NH$_2$, —[N(X)—C$_6$H$_4$]$_{1-3}$—NH—C(=S)—SH, —[N(X)—C$_6$H$_4$]$_{1-3}$—N=CH—Ar—SH, —[N(X)—C$_6$H$_4$]$_{1-3}$—NH—CO—Ar—SH, wherein X is —H, —Z, —CH$_2$—CO—OH, —CH$_2$—CO—O—Z, —CH$_2$—CO—S—Z, —CH$_2$—CO—NH$_2$, —CH$_2$—CO—NH—Z; and Ar is aryl;

each G, independently, is —O—B—R—O—, —NH—B—R—NH—, —O—B—R—NH—, —NH—B—R—

O—, —O—B—R—S—, —NH—B—R—S—, wherein R is $C_{1-30}$ alkyl; B, independently, is —$R_1$—O—[Si(CH$_3$)$_2$—O—]$_{1-100}$, $C_{1-2000}$ alkyl, $C_{6-40}$ aryl, $C_{7-60}$ alkylaryl, $C_{7-60}$ arylalkyl, $(C_{1-30}$ alkyl ether$)_{1-100}$, $(C_{6-40}$ aryl ether$)_{1-100}$, $(C_{7-60}$ alkylaryl ether$)_{1-100}$, $(C_{7-60}$ arylalkyl ether$)_{1-100}$, $(C_{1-30}$ alkyl thioether$)_{1-100}$, $(C_{6-40}$ aryl thioether$)_{1-100}$, $(C_{7-60}$ alkylaryl thioether$)_{1-100}$, $(C_{7-60}$ arylalkyl thioether$)_{1-100}$, $(C_{2-50}$ alkyl ester$)_{1-100}$, $(C_{7-60}$ aryl ester$)_{1-100}$, $(C_{8-70}$ alkylaryl ester$)_{1-100}$, $(C_{8-70}$ arylalkyl ester$)_{1-100}$, —$R_1$—CO—O—$(C_{1-30}$ alkyl ether$)_{1-100}$, —$R_1$—CO—O—$(C_{6-40}$ aryl ether$)_{1-100}$, —$R_1$—CO—O—$(C_{7-60}$ alkylaryl ether$)_{1-100}$, —$R_1$—CO—$(C_{7-60}$ arylalkyl ether$)_{1-100}$, $(C_{4-50}$ alkyl urethane$)_{1-100}$, $(C_{14-60}$ aryl urethane$)_{1-100}$, $(C_{10-80}$ alkylaryl urethane$)_{1-100}$, $(C_{10-80}$ arylalkyl urethane$)_{1-100}$, $(C_{5-50}$ alkyl urea$)_{1-100}$, $(C_{14-60}$ aryl urea$)_{1-100}$, $(C_{10-80}$ alkylaryl urea$)_{1-100}$, $(C_{10-80}$ arylalkyl urea$)_{1-100}$, $(C_{2-50}$ alkyl amide$)_{1-100}$, $(C_{7-60}$ aryl amide$)_{1-100}$, $(C_{8-70}$ alkylaryl amide$)_{1-100}$, $(C_{8-70}$ arylalkyl amide$)_{1-100}$, $(C_{3-30}$ alkyl anhydride$)_{1-100}$, $(C_{8-50}$ aryl anhydride$)_{1-100}$, $(C_{9-60}$ alkylaryl anhydride$)_{1-100}$, $C_{9-60}$ arylalkyl anhydride$)_{1-100}$, $(C_{2-30}$ alkyl carbonate$)_{1-100}$, $(C_{7-50}$ aryl carbonate$)_{1-100}$, $(C_{8-60}$ alkylaryl carbonate)$_{1-100}$, $(C_{8-60}$ arylalkyl carbonate$)_{,1-100}$, —$R_1$—O—CO—NH—($R_2$ or Ar—$R_2$—Ar)—NH—CO—O—$(C_{1-30}$ alkyl ether, $C_{6-40}$ aryl ether, $C_{7-60}$ alkylaryl ether, or $C_{7-60}$ arylalkyl ether$)_{1-100}$, —$R_1$—O—CO—NH—($R_2$ or Ar—$R_2$—Ar)—NH—CO—O—$(C_{2-50}$ alkyl ester, $C_{7-60}$ aryl ester, $C_{8-70}$ alkylaryl ester, or $C_{8-70}$ arylalkyl ester$)_{1-100}$, —$R_1$—O—CO—NH—($R_2$ or Ar—$R_2$—Ar)—NH—CO—O—$(C_{1-30}$ alkyl ether, $C_{6-40}$ aryl ether, $C_{7-60}$ alkylaryl ether, or $C_{7-60}$ arylalkyl ether$)_{1-100}$—CO—NH—($R_2$ or Ar—$R_2$—Ar)—NH—CO—O—, —$R_1$—O—CO—NH—($R_2$ or Ar—$R_2$—Ar)—NH—CO—O—$(C_{2-50}$ alkyl ester, $C_{7-60}$ aryl ester, $C_{8-70}$ alkylaryl ester, or $C_{8-70}$ arylalkyl ester$)_{1-100}$—$R_3$—O—CO—NH—($R_2$ or Ar—$R_2$—Ar)—NH—CO—O—, —$R_1$—NH—CO—NH—($R_2$ or Ar—$R_2$—Ar)—NH—CO—O—$(C_{1-30}$ alkyl ether, $C_{6-40}$ aryl ether, $C_{7-60}$ alkylaryl ether, or $C_{7-60}$ arylalkyl ether$)_{1-100}$, —$R_1$—NH—CO—NH—($R_2$ or Ar—$R_2$—Ar)—NH—CO—$(C_{2-50}$ alkyl ester, $C_{7-60}$ aryl ester, $C_{8-70}$ alkylaryl ester, or $C_{8-70}$ arylalkyl ester$)_{1-100}$, —$R_1$—NH—CO—NH—($R_2$ or Ar—$R_2$—Ar)—NH—CO—O—$(C_{1-30}$ alkyl ether, $C_{6-40}$ aryl ether, $C_{7-60}$ alkylaryl ether, or $C_{7-60}$ arylalkyl ether$)_{1-100}$—CO—NH—($R_2$ or Ar—$R_2$—Ar)—NH—CO—O—, —$R_1$—NH—CO—NH—($R_2$ or Ar—$R_2$—Ar)—NH—CO($C_{2-50}$ alkyl ester, $C_{7-60}$ aryl ester, $C_{8-70}$ alkylaryl ester, or $C_{8-70}$ arylalkyl ester$)_{1-100}R_3$O—CO—NH—($R_2$ or Ar—$R_2$—Ar)—NH—CO—O—, —$R_1$—O—CO—NH—($R_2$ or Ar—$R_2$—Ar)—NH—CO—NH—($C_{2-50}$ alkyl amide, $C_{7-60}$ aryl amide, $C_{8-70}$ alkylaryl amide, or $C_{8-70}$ arylalkyl amide$)_{1-100}$, or —$R_1$—NH—CO—NH—($R_2$ or Ar—$R_2$—Ar)—NH—CO—NH—($C_{2-50}$ alkyl amide, $C_{7-60}$ aryl amide, $C_{8-70}$ alkylaryl amide, or $C_{8-70}$ arylalkyl amide$)_{1-100}$; wherein each of $R_1$, $R_2$, and $R_3$, independently, is $C_{1-30}$ alkyl; and Ar is aryl; and a pharmaceutically acceptable carrier.

30. The pharmaceutical composition of claim 29, wherein a is an integer of 2–6.

31. The composition of claim 30, wherein b is 0; c is 1; and n is 2.

32. The composition of claim 31, wherein p is 0; a is 4; m is an integer of 1–8; $F_1$ is $C_{60}$ fullerene; and A is tetraaniline of the emeradine base form, substituted at the nitrogen atom of each benzenoid unit with —$C_3H_6SO_3$Na or —$C_4H_8SO_3$Na.

33. The composition of claim 29, wherein b is 1.

* * * * *